(12) United States Patent
Hirayama

(10) Patent No.: US 8,958,990 B2
(45) Date of Patent: Feb. 17, 2015

(54) SAMPLE ANALYZER AND SAMPLE ANALYZING METHOD

(75) Inventor: Hideki Hirayama, Akashi (JP)

(73) Assignee: Sysmex Corporation, Kobe (JP)

(*) Notice: Subject to any disclaimer, the term of this patent is extended or adjusted under 35 U.S.C. 154(b) by 912 days.

(21) Appl. No.: 11/542,312

(22) Filed: Oct. 3, 2006

(65) Prior Publication Data

US 2007/0111197 A1    May 17, 2007

(30) Foreign Application Priority Data

Oct. 3, 2005  (JP) ................................. 2005-290250
Oct. 3, 2005  (JP) ................................. 2005-290251

(51) Int. Cl.
*G01N 33/48* (2006.01)
*G01N 31/00* (2006.01)
*G06G 7/48* (2006.01)
*G06G 7/58* (2006.01)
*G06F 19/00* (2011.01)
*G06Q 50/24* (2012.01)

(52) U.S. Cl.
CPC .............. *G06F 19/363* (2013.01); *G06Q 50/24* (2013.01)
USPC .................... 702/19; 702/22; 703/11; 703/12

(58) Field of Classification Search
CPC ............. G01N 35/00603; H04L 69/28; G11B 2020/1823
See application file for complete search history.

(56) References Cited

U.S. PATENT DOCUMENTS

| | | | |
|---|---|---|---|
| 4,761,075 A * | 8/1988 | Matsushita et al. | 356/39 |
| 5,047,321 A * | 9/1991 | Loken et al. | 435/6.11 |
| 6,148,286 A * | 11/2000 | Siegel | 704/270 |
| 6,391,263 B1 * | 5/2002 | Mishima et al. | 422/67 |
| 6,631,211 B1 * | 10/2003 | Schermer et al. | 382/225 |
| 6,635,488 B1 * | 10/2003 | Saito et al. | 436/43 |
| 2003/0070498 A1 | 4/2003 | Ohyama et al. | |
| 2005/0053521 A1 | 3/2005 | Hirayama | |

\* cited by examiner

*Primary Examiner* — Larry D Riggs, II
(74) *Attorney, Agent, or Firm* — Brinks Gilson & Lione

(57) ABSTRACT

A sample analyzer comprising: a measurement section for measuring a sample of an animal; a memory for storing a measurement data by the measurement section; an analysis section for analyzing the measurement data stored on the memory in accordance with a first analysis condition corresponding to a previous setting of a species of an animal; and a selection receiver for receiving a selection of a species of an animal, which is different from the species of the previous setting, after analyzing the measurement data by the analysis section; wherein the analysis section analyzes the measurement data stored on the memory in accordance with a second analysis condition corresponding to the selection of a species of an animal when the selection receiver receives the selection of a species of an animal, is disclosed. A sample analyzing method is also disclosed.

19 Claims, 20 Drawing Sheets

SAMPLE ANALYZER AND SAMPLE ANALYZING METHOD

This application claims priority under 35 U.S.C. §119 to Japanese Patent Application No. 2005-290250 filed Oct. 3, 2005 and Japanese Patent Application No. 2005-290251 filed Oct. 3, 2005, the entire content of which is hereby incorporated by reference.

FIELD OF THE INVENTION

The present invention relates a sample analyzer for analyzing samples of a plurality of species of animals and a sample analyzing method for a plurality of species of animals.

BACKGROUND

Recently, veterinaries and livestock testing facilities have been conducting analyses of biological samples of animals such as blood and urine. Analyses of such biological samples are performed using analyzers such as those described in, for example, US Laid-Open Patent Publication Nos. 2005/0053521 and 2003/0070498. Since a wide variety of animal species are dealt with in these veterinaries and livestock testing facilities, these analyzers need to be capable of performing analyses of a plurality of animal species. The analyzers disclosed in the above mentioned patent publications allow selection of an animal species, and are capable of analyzing biological samples under analysis conditions that conform to the selected animal species.

The properties of biological samples such as blood and urine differ markedly by species. Therefore, accurate analysis results can not be obtained unless a biological sample is analyzed under analysis parameters that are appropriate for the animal species of the analysis object. In these analyzers, however, since an animal species can not be changed after a single animal species is selected and analysis starts, the same sample can not be reused for analysis when the wrong species of animal has been erroneously selected. Particularly in the case of small animals, since large quantities of a biological samples such as blood and urine can not be collected, nor can excessive stress be put on the living body of small animals to collect a biological sample several times, it becomes necessary to avoid wastefully consuming the valuable biological samples. Furthermore, there is the additional problem of the excess labor required since reanalysis must be performed after collecting the biological sample.

SUMMARY

The scope of the present invention is defined solely by the appended claims, and is not affected to any degree by the statements within this summary.

A first aspect of the present invention is a sample analyzer comprising: a measurement section for measuring a sample of an animal; a memory for storing a measurement data by the measurement section; an analysis section for analyzing the measurement data stored on the memory in accordance with a first analysis condition corresponding to a previous setting of a species of an animal; and a selection receiver for receiving a selection of a species of an animal, which is different from the species of the previous setting, after analyzing the measurement data by the analysis section; wherein the analysis section analyzes the measurement data stored on the memory in accordance with a second analysis condition corresponding to the selection of a species of an animal when the selection receiver receives the selection of a species of an animal.

A second aspect of the present invention is a sample analyzer comprising: a measurement section for measuring a sample of an animal; a memory for storing a measurement data by the measurement section; a selection receiver for receiving a selection of a species of an animal after a measurement of the sample by the measurement section; and an analysis section for analyzing the measurement data stored on the memory in accordance with an analysis condition corresponding to the selection of a species of an animal received by the selection receiver.

A third aspect of the present invention is a sample analyzer comprising: measuring a sample of an animal; analyzing a measurement data of the sample in accordance with a first analysis condition corresponding to a previous setting of a species of an animal; receiving a selection of a species of an animal, which is different from the species of the previous setting, after analyzing the measurement data; and reanalyzing the measurement data in accordance with a second analysis condition corresponding to the selection of a species of an animal.

DETAILED DESCRIPTION OF THE PREFERRED EMBODIMENTS

The preferred embodiments of the present invention are described hereinafter with reference to the drawings.

Figure 1:
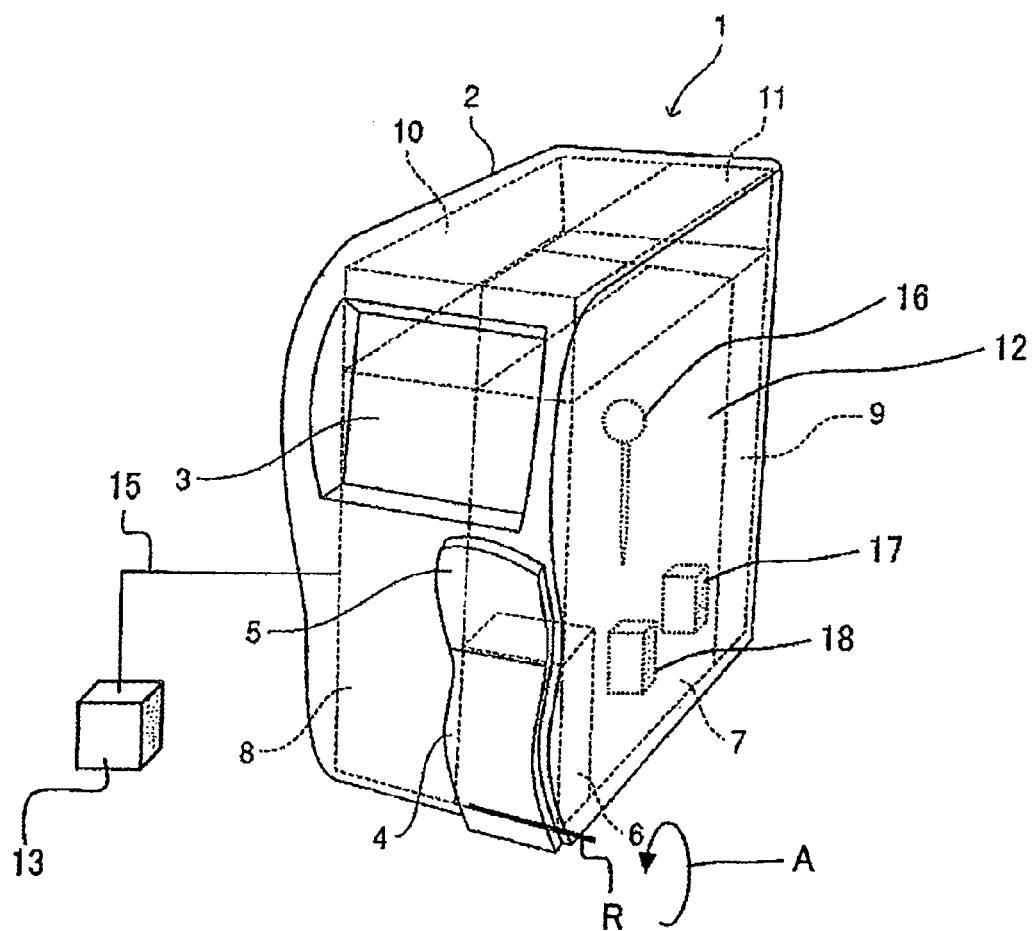
FIG. 1 is a perspective view briefly showing the structure of a biological sample analyzer of an embodiment of the present invention.

FIG. 1 is a perspective view briefly showing the structure of a biological sample analyzer of an embodiment of the present invention. The biological sample analyzer 1 is a blood cell counter that counts red blood cells and white blood cells and the like of animal species such as dog, cat, cow, horse and the like. The biological sample analyzer 1 is capable of operating in operation modes that correspond to each species of animal, such as a dog analysis mode for analyzing the blood of dogs, cat analysis mode for analyzing the blood of cats and the like.

As shown in FIG. 1, the biological sample analyzer 1 is provided with a housing 2, display 3, sample setting panel 4, button 5, controller 9, power source 10, printer 11, and measuring mechanism 12. The housing 2 is an approximately rectangular shaped box, which internally accommodates the display 3, controller 9, power source 10, printer 11, and measuring mechanism 12. The display 3 is a touch panel type liquid crystal display that is mounted on the upper front surface of the housing 2. Information can be display and user input can be received via the display 3. Below the display 3 of the housing 2 is hollowed, and this hollow part is closed by a door-like sample setting panel 4. The bottom end of the sample setting panel 4 pivots on an axle R that extends in the lateral direction of the housing 2, and the sample setting panel 4 is rotatable in a forward direction (arrow A direction in the drawing) via the axle R. The button 5 is disposed above the sample setting panel 4, and the sample setting panel 4 and the button 5 are mutually connected. When a user presses the button 5, the connection of the sample setting panel 4 and the button 5 is released, and the sample setting panel 4 rotates forward. Furthermore, when the sample setting panel 4 is in an opened condition and the user presses the panel 4 backward, the sample setting panel 4 and the button 5 are reconnected via the rotation, such that the sample setting panel 4 maintains a closed condition.

A sample setting unit 6 is provided at the back part of the sample setting panel 4. The sample setting unit 6 has an open top to allow a sample container that contains a sample (biological sample) to be placed within the unit through the open top. The sample setting unit 6 rotates integratedly with the sample setting panel 4, such that a user can place a sample container in the sample setting unit 6. A user who has placed a sample container presses the sample setting panel 4 backward so as to return the sample setting unit 6 to the closed position shown in FIG. 1. Thus, a sample can be measured.

The measuring mechanism 12 is provided with a sample processing part 7 and a fluid controller 8. The sample processing part 7 is provided with a suction mechanism 16, detecting part 17, and mixing chamber 18. The suction mechanism 16 suctions the sample from the sample container placed in the sample setting part 6 and injects the sample into the detecting part 17 and mixing chamber 18; the mechanism is provided with a suction tube and a motor or the like for moving the suction tube. The fluid controller 8 is connected to a reagent container 13 that contains reagent via a tube 15, and is provided with a pump for delivering the reagent, and a motor or the like for actuating the pump. The sample and reagent are injected into the detecting part 17 and mixing part 18, and a discharged therefrom, via the fluid controller 8. The mixing chamber 18 is used to adjust the measurement sample by mixing the sample and reagent, and the sample that has been adjusted by the mixing chamber 18 is supplied to the detecting part 17. The detecting part 17 detects blood cells by a well known electrical resistance detection method, and outputs electrical signals that represent the characteristics of the blood cells in the sample. Furthermore, the detecting part 17 detects the opacity (light absorption) of the sample by a well known optical detection method, and outputs electrical signals representing this opacity. Specifically, the detecting part 17 outputs electrical signals representing white blood cells, red blood cells, hemoglobin, and platelets contained in the sample. These output signals are sent to the controller 9, which processes these signals to obtain data representing the size (volume) of each detected particle (blood cell), and data representing the opacity (light absorption) of the sample as measurement data. The controller 9 controls the operation of each of these units and calculates the analysis results. The power supply 10 converts the alternating current (AC) from a commercial AC power source to a direct current (DC), and supplies this direct current to the controller 9 and motors and the like of each unit. The printer 11 receives instructions from the controller 9 and prints the analysis results and the like.

Figure 2:
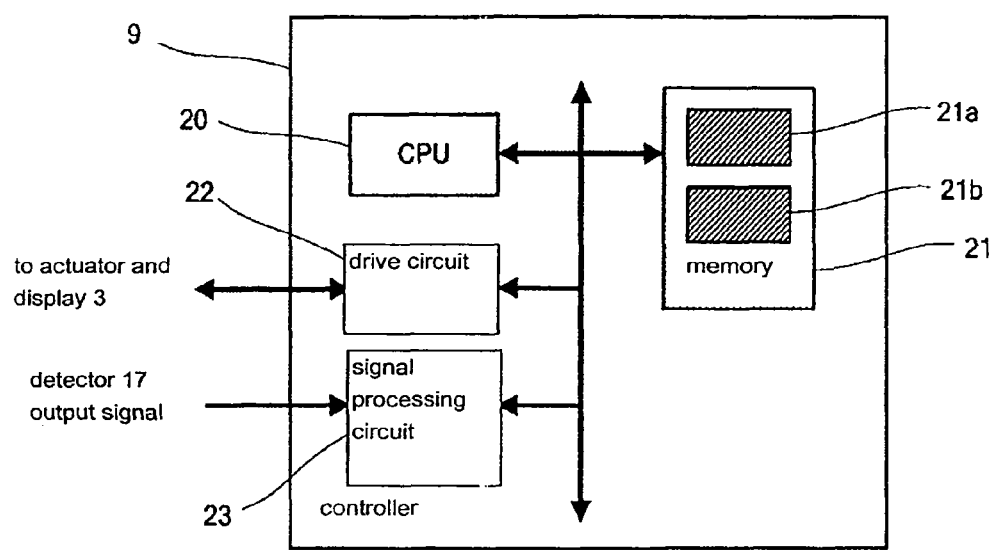
FIG. 2 shows the structure of the control unit.

The structure of the controller 9 is described in detail below. FIG. 2 shows the structure of the controller 9. The controller 9 is provided with a CPU 20, memory 21, drive circuit 22, and signal processing circuit 23. The CPU 20 is capable of executing programs stored in the memory 21, and the biological sample analyzer 1 is operated in a manner described later when the CPU 20 executed these programs. The memory 21 is configured, for example, by RAM such as SRAM, DRAM or the like, ROM such as a mask ROM, EEPROM or the like, flash memory (registered trademark) or the like; the memory 21 contains pre-stored programs, stores data generated during program execution, and stores measurement data and analysis results and the like. The memory 21 contains two areas: area 21a and area 21b.

The area 21a stores an application program for overall control of the biological sample analyzer 1, a measurement control program for controlling the measurement operation and controlling the operation of the motors and the like of the fluid controller 8 and suction mechanism 16, and analysis program for obtaining analysis results by analyzing measurement data obtained by signal processing the electrical signals output from the detection part 17. The area 21b is used jointly by these programs. The area 21b stores analysis result data D which represent the analysis results obtained by the biological sample analyzer 1. The analysis result data are obtained for each sample and stored in the area 21b for a predetermined number of samples (for example, twenty samples) sequentially from the newest. The analysis result data D include measurement data D1 obtained by signal processing the electrical signals detected by the detecting part 17, and analysis result data D2 representing the analysis results of the analysis program.

The drive circuit 22 receives the instructions from the measuring operation program, and controls the actuation of the motors, actuators such as a electromagnetic valves (not shown in the drawing, and display 3. The signal processing circuit 23 performs predetermined signal processing, for example, noise elimination process, A/D conversion processing, high pulse detection processing and the like on the electrical signals obtained by the detecting part 17, and outputs the measurement data D1 as digital data. The obtained measurement data D1 are intermediate data representing the properties of the sample until arriving at the analysis data D2, and are stored in the area 21b of the memory 21.

Figure 3:
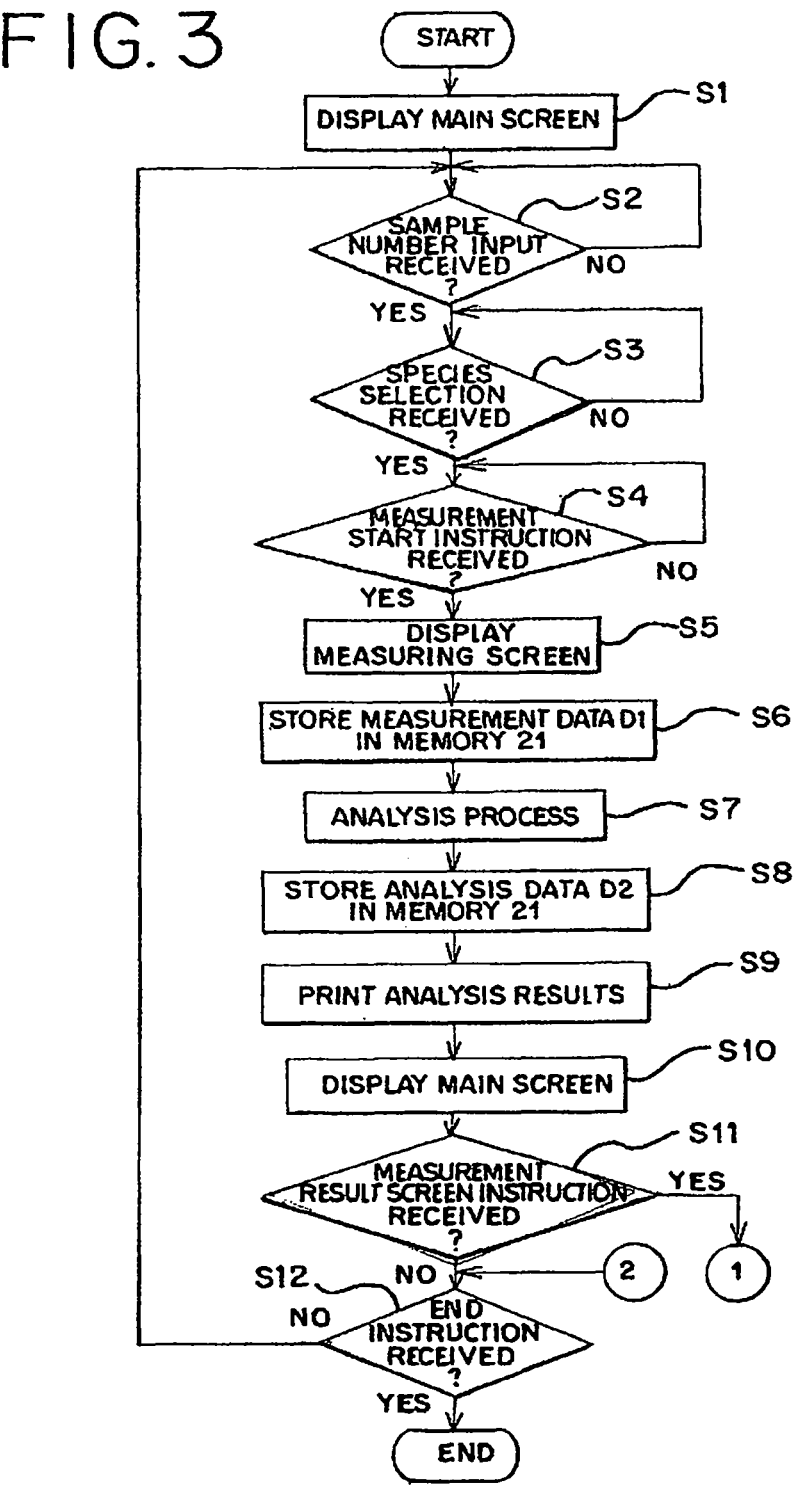
FIGS. 3 and 4 are flow charts showing the operation flow of the biological sample analyzer of the embodiment of the present invention.
Figure 4:
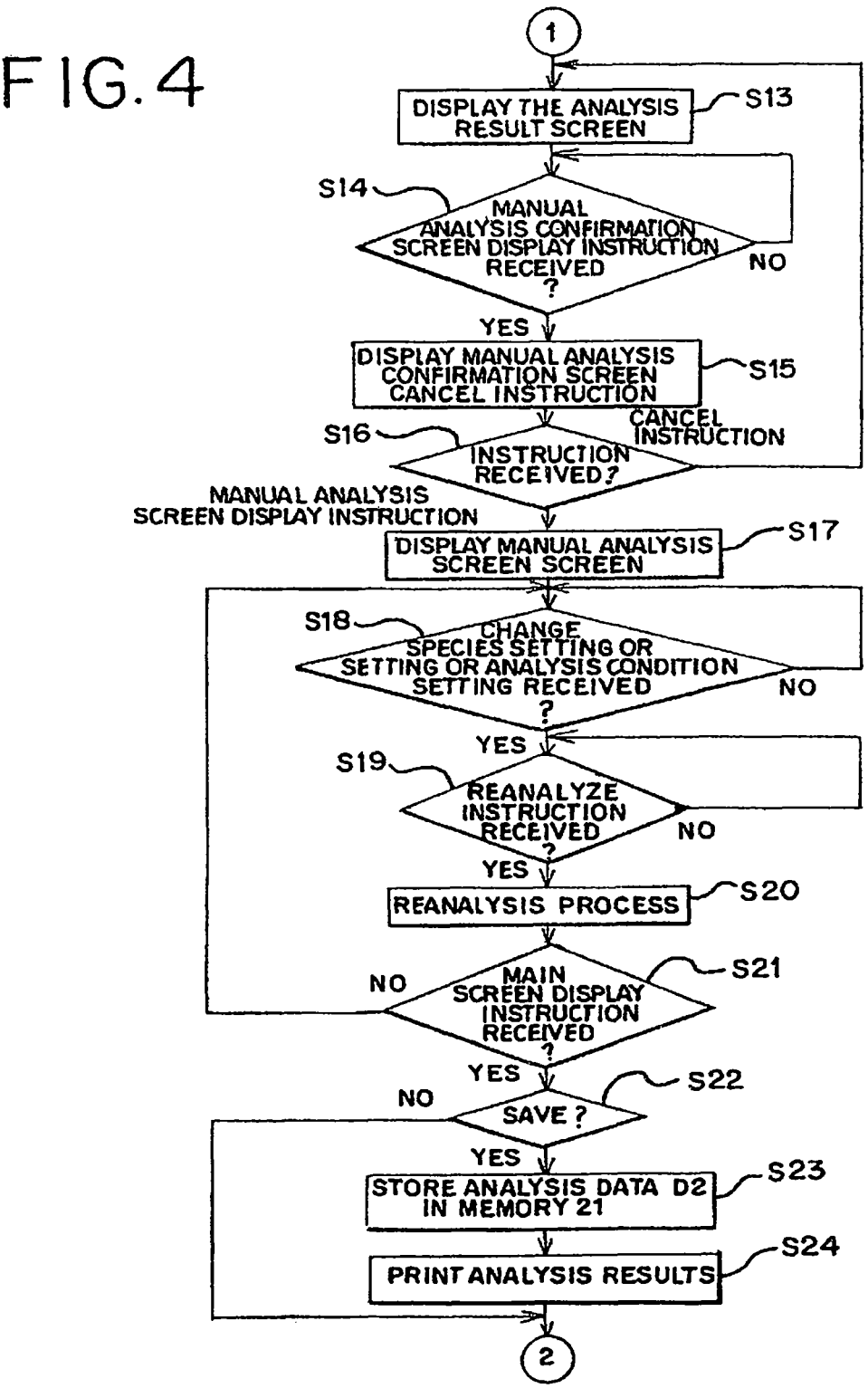
Figure 5:
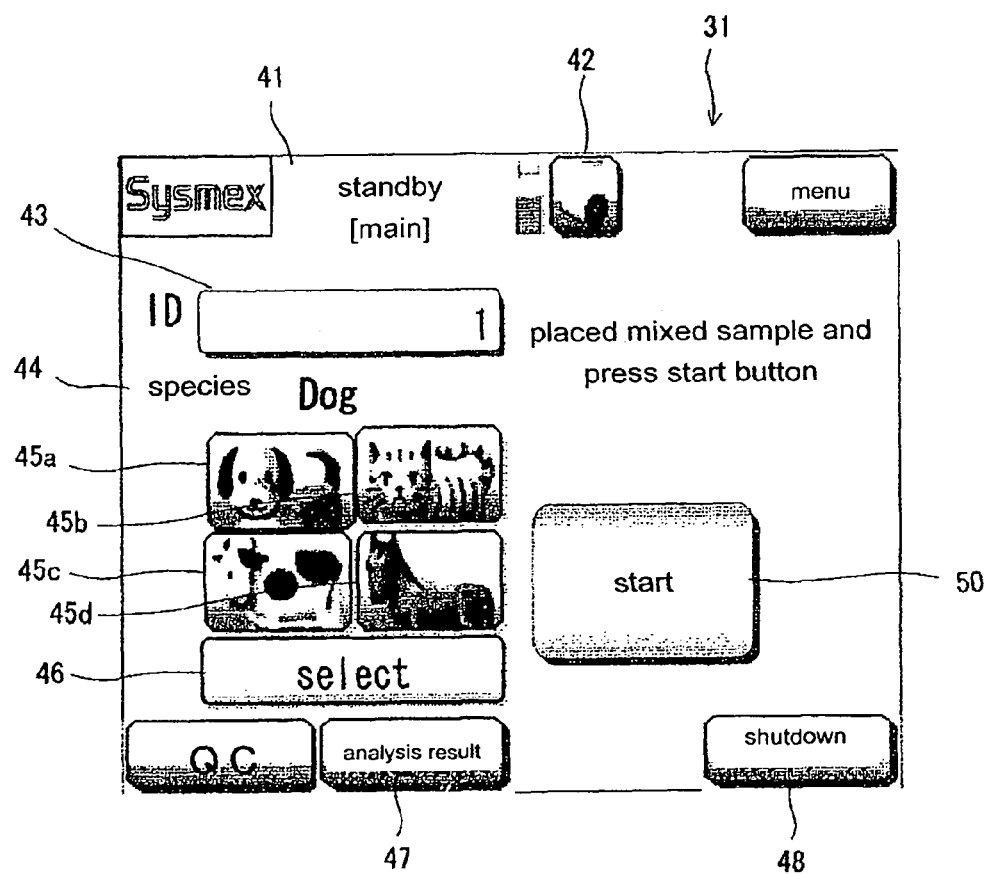
FIG. 5 shows a main screen.

The operation of the biological sample analyzer 1 of the embodiment of the present invention is described below. FIGS. 3 and 4 are flow charts showing the operation flow of the biological sample analyzer 1 of the embodiment of the present invention. First, the user starts the biological sample analyzer 1. Immediately after start-up, the controller 9 displays the main screen on the display 3 (step S1). FIG. 5 shows a main screen. The main screen 31 is provided with an analyzer status display area 41, paper feed button 42, sample number display area 43, animal species display area 44, animal species selection icons 45a through 45d, selector button 46, analysis result button 47, shutdown button 48, start button 50 and the like. At this time, the message "standby" is displayed on the analyzer status display area 41 since a sample was not first placed in the biological sample analyzer 1. This "standby" display indicates that the measurement can start. In this condition in which the main screen is displayed, a user presses the button 5, the sample setting panel 4 rotates forward, and a sample is placed in the sample setting unit 6. Then, the user rotates the sample setting panel 4 backward until the sample setting panel 4 engages the button 5 such that the sample is set in the biological sample analyzer 1.

Next, the controller 9 receives the sample number input by the user (step S2: YES). The sample number input is accomplished as follows. When the user touches the sample number display area 1 of the main screen 31 with a fingertip, a software keyboard is displayed on the display 3. The user can input the sample number by touching the software keys with a fingertip. Then, the controller 9 selects the measurement animal species, that is, receives the setting for the operating mode (step S3: YES). The animal species selection icon 45a on the main screen 31 is assigned to dog, 45b is assigned to cat, 45c is assigned to cow, 45d is assigned to horse, and the assigned animal species is illustrated in each icon. Although a picture of the animal species is shown in the icons in FIG. 5, the illustration is not limited to this mode inasmuch as, for example, text may be displayed to indicate the animal species. If the animal species object is shown in one of the four icons, the user touches that animal species icon with a fingertip. Thus, that animal species is set as the measurement object (measurement animal species). At this time, the icon of the set measurement animal species is displayed in a different way than the other icons, such as only the icon of the set as the measurement animal species is displayed in color and the other icons are displayed in black and white so as to allow the user to easily confirm which species has been set as the measurement species.

Figure 6:
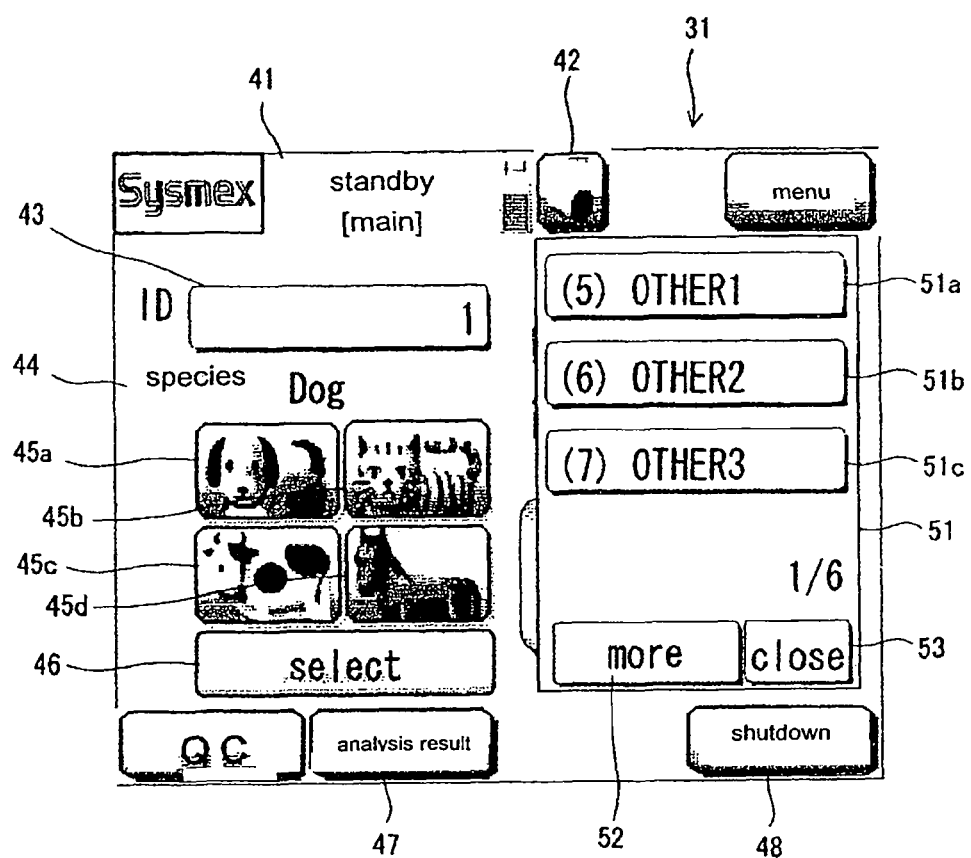
FIG. 6 shows a screen that displays the measurement object species selection dialogue.

Furthermore, the user performs the following operation to select an animal species that is not represented by one of the four icons as a measurement animal species. First, the user touches the selector button 46 with a fingertip. When the selector button 46 is selected in this way, a measurement species selection dialogue is displayed. FIG. 6 shows a screen that displays the measurement species selection dialogue. A plurality of buttons 51a through 51c used for animal species selection are aligned and displayed in the measurement species selection dialogue 51. A page switching button 52 and close button 53 are also displayed in the measurement species selection dialogue 51. The buttons 51a through 51c can be allocated to optional animal species by the user, and the name of the allocated animal species can be displayed. In the example shown in FIG. 6, the user has not made any allocations, and the buttons 51a through 51c are displayed as "OTHER 1," "OTHER 2," and "OTHER 3." When one of these buttons 51a through 51c is selected, the controller 9 sets the animal species allocated to the selected button as the measurement species. That is, the desired species of animal is set as the measurement species when the user touches the button of the desired species with a fingertip in the dialogue 51. The measurement species selection dialogue 51 is configured by a plurality of pages, such that when the page switching button 52 is selected, the controller 9 switches the display to another page. Therefore, when the button of a desired species is not displayed on the page, the user touches the page switching button 52 with a fingertip, and the display is switched to another page. Furthermore, when the close button 53 is selected, the dialogue 51 is closed.

The process for setting the animal species and analysis conditions of animal species for the buttons 51a through 51c is described below.

Figure 14:
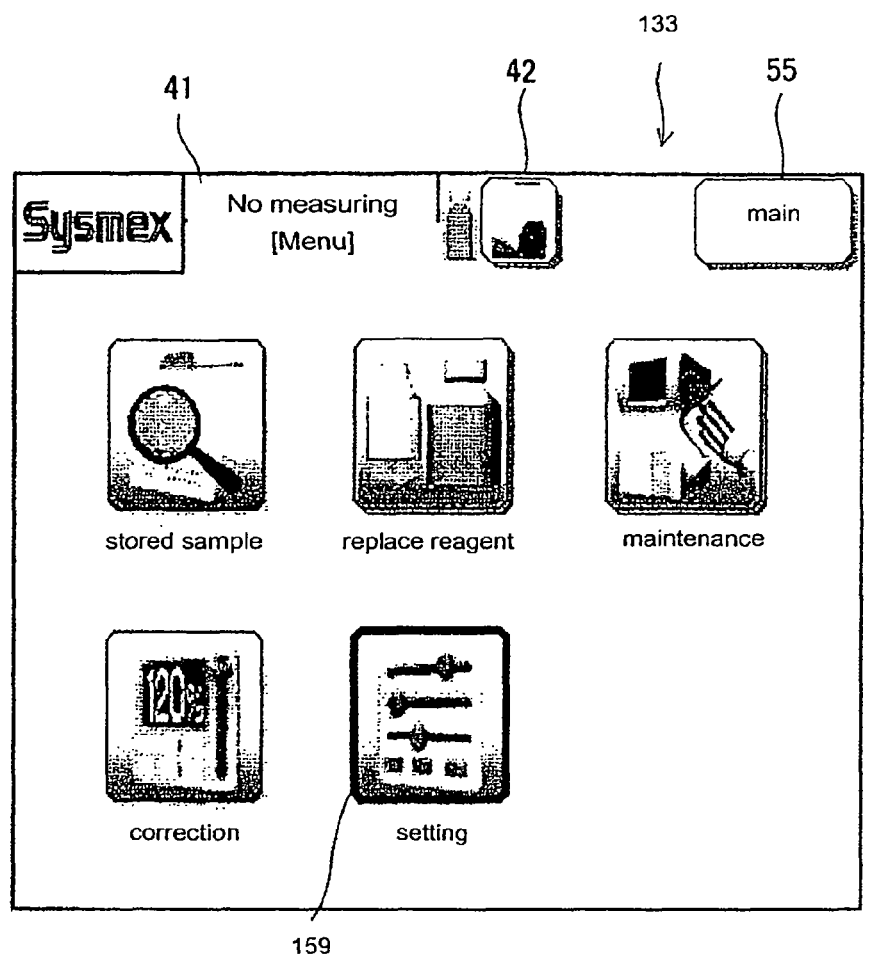
FIG. 14 shows a menu screen.
Figure 15:
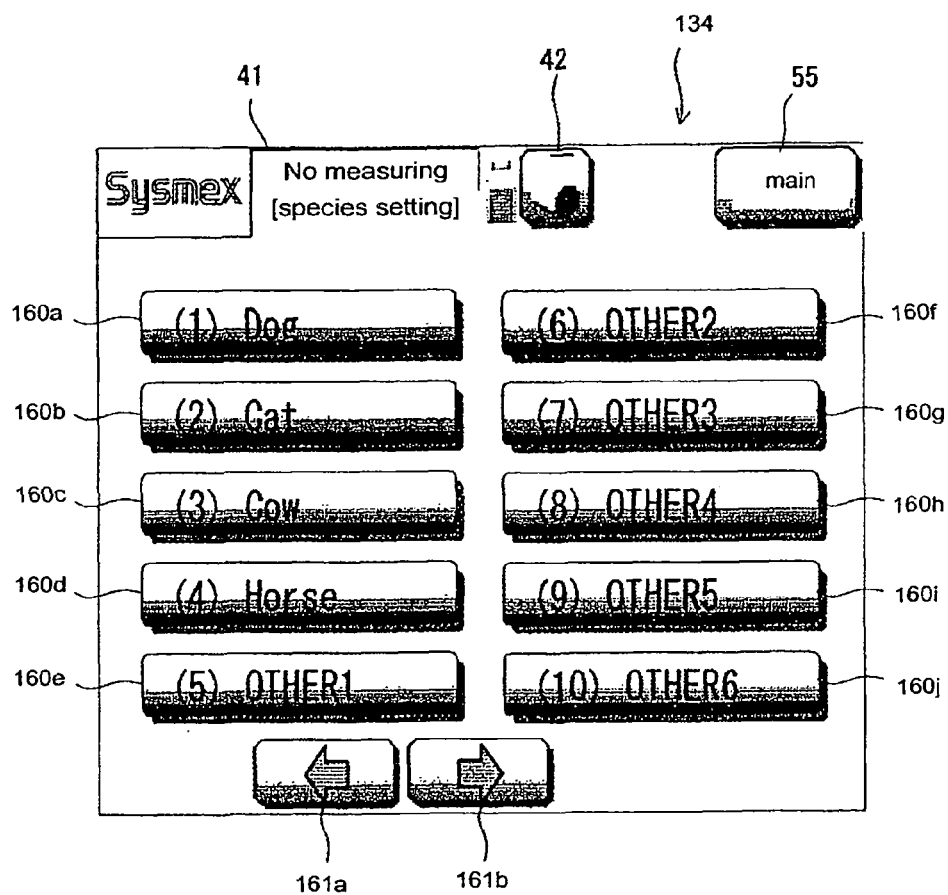
FIG. 15 shows an example of a first screen for species selection.

FIG. 15 shows an example of a first screen for species selection. This screen is displayed by selecting the setting button 159 displayed in the menu screen 133 shown in FIG. 14. As shown in FIG. 15, the first animal species selection screen 134 is provided with an analyzer status display area 41, paper feed button 42, and main screen call button 55, and also provided with ten species buttons 160a through 160j that respectively correspond to various species, and change screen buttons 161a and 161b. The species button 160a is allocated for dog and displays "Dog." Similarly, the species buttons 160b, 160c, and 160d are respectively allocated for cat, cow, and horse, and respectively display "Cat," "Cow," and "Horse." The species buttons 160e through 160j are user-allocatable for optional species, and display the name of the allocated species. In the example shown in FIG. 15, the user has not allocated these buttons, such that the buttons 160e through 160j display "Other 1," "Other 2," and "Other 3." When a user touches the change screen buttons 161a and 161b with a fingertip in the first species selection screen 134, a second species selection screen is displayed.

Figure 16:
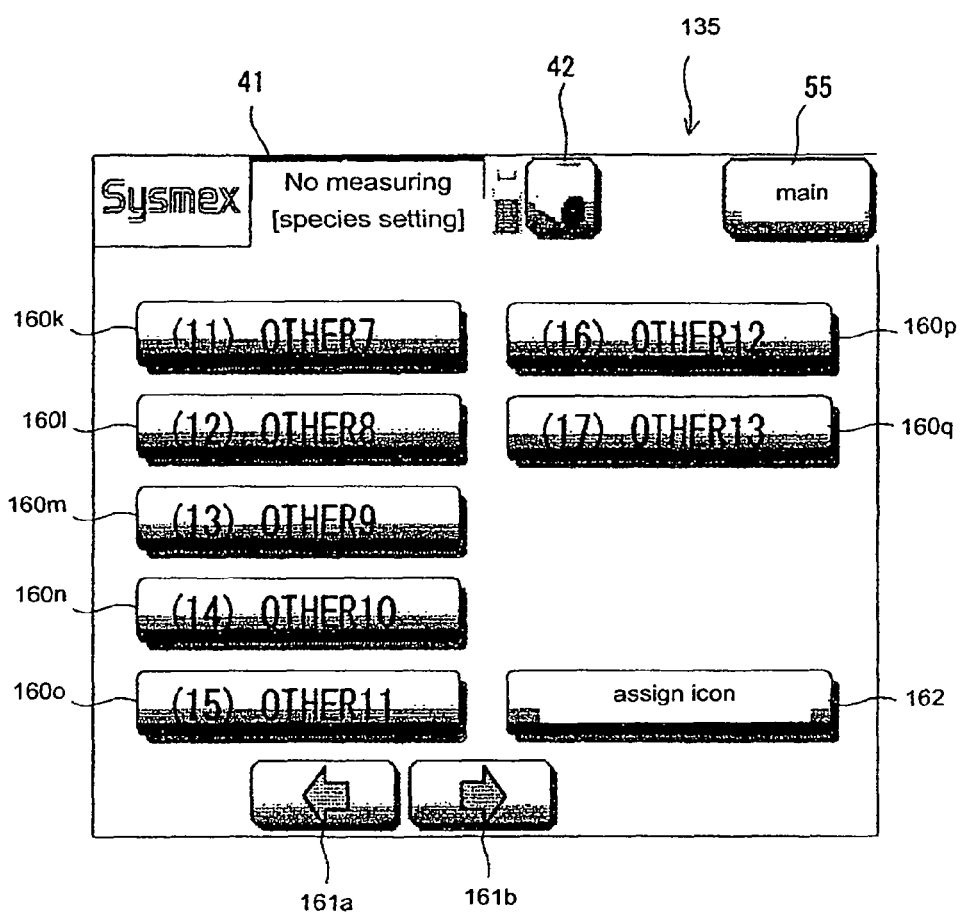
FIG. 16 shows a second screen for species selection.

FIG. 16 shows a second species selection screen. As shown in the drawing, the second species selection screen 135 is provided with an analyzer status display area 41, paper feed button 42, main screen call button 55, and change screen buttons 161a and 161b, as well as seven species buttons 160k through 160q, and an icon allocation button 162. The species buttons 160k through 160q are user-allocatable for optional species, and display the name of the allocated species. In the example shown in FIG. 16, the user has not allocated these buttons, such that the buttons 160k through 160q display "Other 7," "Other 8," and "Other 9." Furthermore, when the change screen buttons 161a and 161b are selected, the display is switched to the previously described first species selection screen 134.

When changing the setting of the analysis condition of a species, the user selects the species button among buttons 160a through 160q corresponding to the species of the desired setting change in the first species selection screen 134 and the second species selection screen 135, and the icon allocation button 162 is selected when changing the setting of the species selection icons 45a through 45d.

Figure 17:
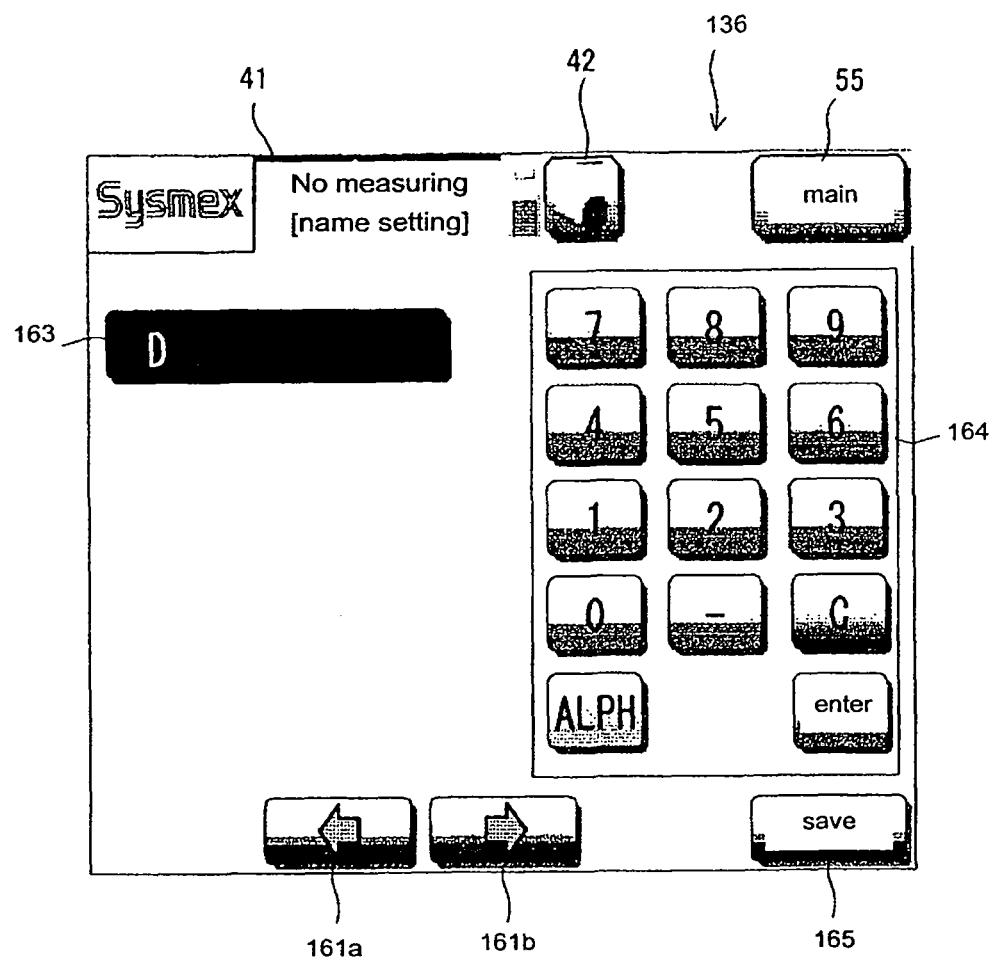
FIG. 17 shows a species name setting screen.

The analysis condition changing process is described in detail below. When changing the setting of the analysis conditions for dog, cat, cow, and horse, the user touches one of the animal species buttons 160a, 160b, 160c, or 160d with a fingertip. Thus, a first abnormality setting screen for the species corresponding to the selected button is displayed. The first abnormality setting screen is described later. When setting the analysis condition of another species, the user touches any one button among the species buttons 160e through 160q with a fingertip. Thus, the species name setting screen corresponding to the selected button is displayed on the display 3. FIG. 17 shows a species name setting screen. As shown in the drawing, the species name setting screen 136 is, similar to the first species selection screen, provided with an analyzer status display area 41, paper feed button 42, main screen call button 55, and change screen buttons 161a and 161b, as well as a text input display area 163, software keyboard 164, and save button 165. A user can input text (species name) using the software keyboard 164 in the species name setting screen 136. For example, when setting the analysis conditions for rabbit, the user inputs "Rabbit." The text entered in this way is displayed in the text input display area 163. When the input content is saved, the user touches the save button 165 with a fingertip. Thus, the controller 9 associates the input text with the species button and stores the input text in the memory 21. The analysis condition setting screen is also provided with a first abnormality setting screen, second abnormality setting screen, third abnormality setting screen, fourth abnormality setting screen, fifth abnormality setting screen, correction value setting screen, first, threshold setting screen, and second threshold setting screen. As shown in the drawing, a left pointing arrow is displayed in the change screen button 161a, and a right pointing arrow is displayed in the change screen button 161b. The display on the display 3 is changed to another analysis condition setting screen whenever the user touches the change screen button 161a and 161b with a fingertip. The user presses selects the change screen buttons 161a and 161b until the desired analysis condition setting screen is displayed.

Figure 18:
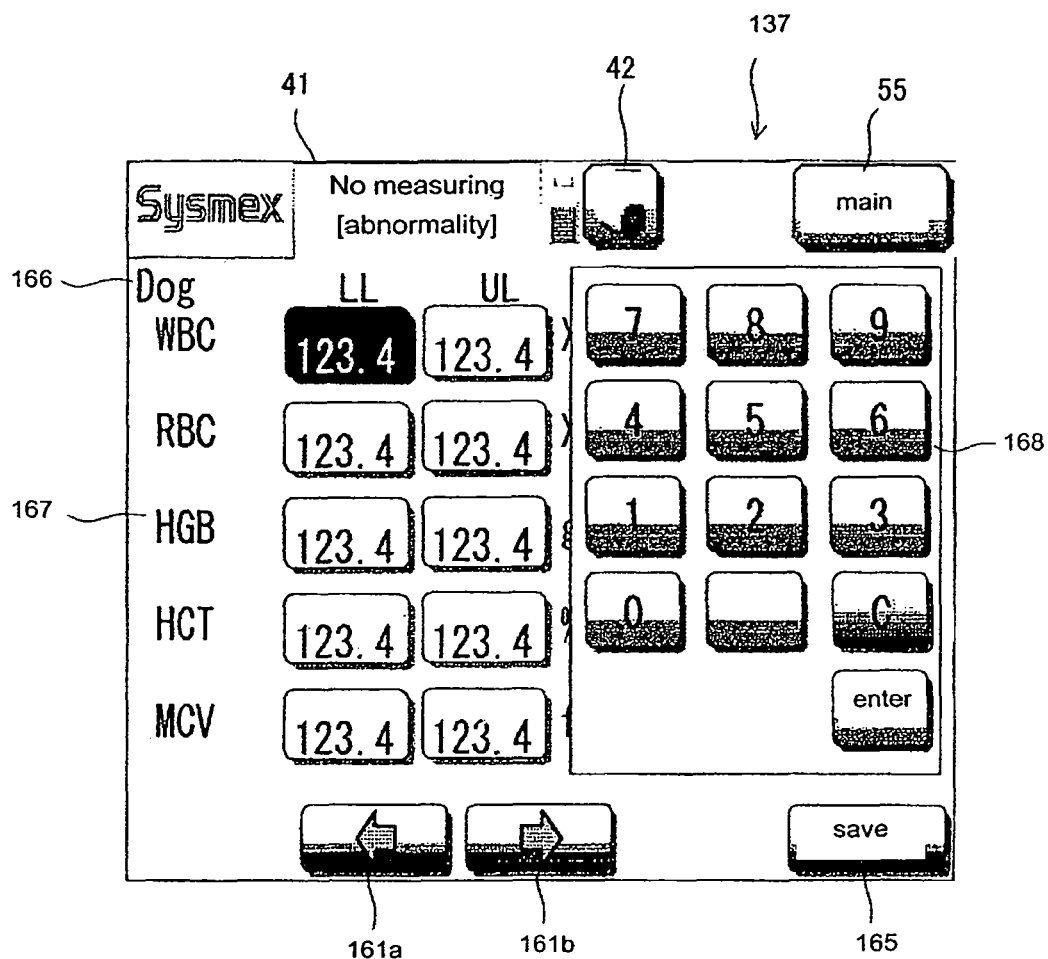
FIG. 18 shows a first screen for determining an abnormality.

FIG. 18 shows a first screen for determining an abnormality. As shown in the drawing, the first abnormality setting screen 137 is, similar to the species name setting screen 136, provided with an analyzer status display area 41, paper feed button 42, main screen call button 55, and change screen buttons 161a and 161b, as well as a species display area 166, and abnormality value display area 167. In the first abnormality setting screen 137, it is possible to set an abnormality for white blood cell concentration (WBC), red blood cell concentration (RBC), hemoglobin concentration (HGB), hematocrit value (HCT), and mean red blood cell volume (MCV). Abnormalities can be set for mean corpuscular cell hemoglobin (MCH), mean corpuscular hemoglobin concentration (MCHC), and platelet concentration (PLT) in the second abnormality screen, abnormalities can be set for small white cell ratio (W-SCR), medium white cell ratio (W-MCR), and large white cell ratio (W-LCR) in the third abnormality setting screen, abnormalities can be set for small white cell concentration (W-SCC), medium white cell concentration (W-MCC), and large white cell concentration (W-LCC) in the fourth abnormality setting screen, and abnormalities can be set for red cell distribution range SD (RDW-SD), red cell distribution range CV (RDW-CV), platelet distribution range (PDW), mean platelet volume (MPV), and large platelet ratio (P-LCR) in the fifth abnormality setting screen. Setting the abnormality is accomplished by setting an upper limit value and lower limit value for a normal analysis value. That is, when an analysis value does not lie between the upper limit value and the lower limit value, the analysis value is deemed abnormal and a flag indicating an abnormality is displayed. The user selects an area by touching the area displaying a set value the user wants to change with a fingertip. When a set value area is selected, the software keyboard 168 is displayed, and the user can enter a new set value via the software keyboard 168. The input set value is displayed in the selected area to indicate the set value has been changed. The software keyboard 168 is not provided with an alphabetic software keys so that only numerals can be entered. After the abnormality setting has been changed in this way, the user saves the setting value by selecting the save button 165. Thus, the controller 9 stores the set value as an abnormality setting of the object animal species in the memory 21.

Figure 19:
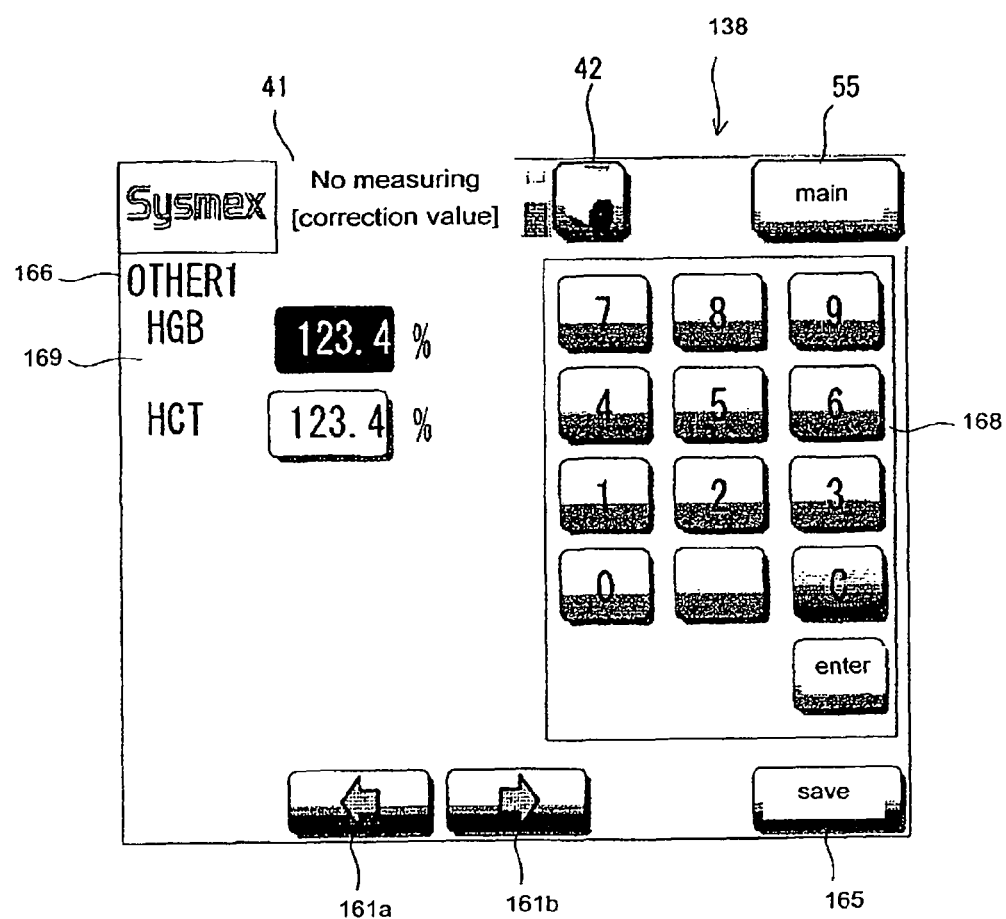
FIG. 19 shows a correction value setting screen.

FIG. 19 shows a correction value setting screen. As shown in the drawing, the correction value setting screen 138 is, similar to the abnormality setting screen 137, provided with an analyzer status display area 41, paper feed button 42, main screen call button 55, change screen buttons 161a and 161b, save button 165, and species display area 166, as well as a correction value display area 169. The correction value can be set for hemoglobin concentration (HGB), and hematocrit value (HCT) in the correction value setting screen 138. The area is selected when the user touches the area displaying the correction value the user wants to change with a fingertip. When a correction value area is selected, a software keyboard 169 is displayed, and the user can input a new correction value via the software keyboard 169. The input correction value is displayed in the selected area to indicate that the correction value has been changed. After the correction value setting has been changed in this way, the user stores the correction value by selecting the save button 165. Thus, the controller 9 stores the correction value as the correction value of the object animal species in the memory 21.

Figure 20:
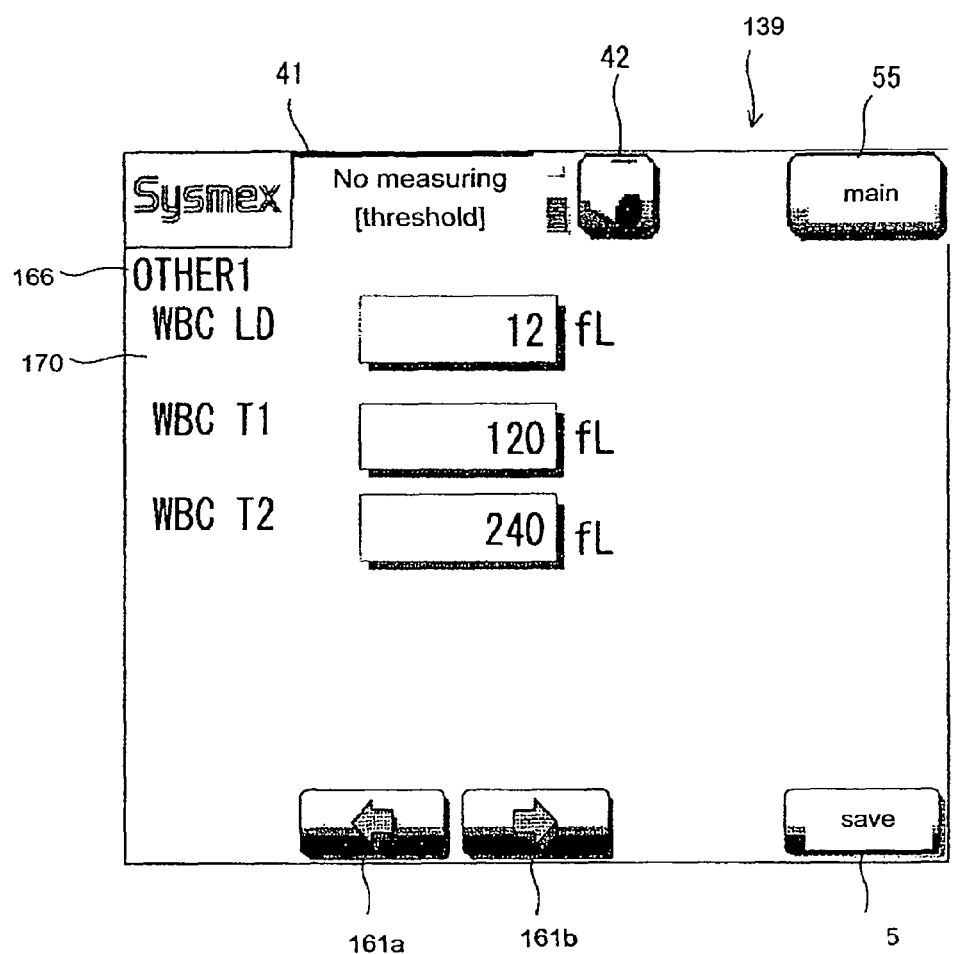
FIG. 20 shows a first screen for setting the threshold.

FIG. 20 shows a first screen for setting the threshold. As shown in the drawing, the first threshold setting screen 139 is, similar to the first abnormality setting screen 137, provided with an analyzer status display area 41, paper feed button 42, main screen call button 55, change screen buttons 161a and 161b, save button 165, and species display area 166, as well as a threshold value display area 170. It is possible to set the white cell thresholds LD, T1, and T2 in the first threshold setting screen 138. Furthermore, the red cell threshold and platelet threshold can be set in the second threshold setting screen. The user selects an area by touching the area displaying the setting value the user wants to change with a fingertip. When the setting value area is selected, a software keyboard (not shown in the drawing) is displayed, and the user can enter a new setting value via the software keyboard. The input setting value is displayed in the selected area to indicate the setting value has been changed. After the setting value has been changed in this way, the user stores the setting value by selecting the save button 165. Thus, the controller 9 stores the setting value as the threshold of the object species in the memory 21. Among the species for which setting values have been stored, the analysis processing is performed using the threshold. Among the four species of dog, cat, cow, and horse (or three species of dog, cat, and cow), the trough position of the particle size distribution is searched from a predetermined range, and this trough position is used as the threshold. The species that can be set in the present embodiment are not limited inasmuch as these species may be, for example, pig, goat, mouse, and rabbit.

Thus, after the settings of the analysis condition have been changed, the user calls the main screen by touching the main screen call button 55 with a fingertip.

Figure 7:
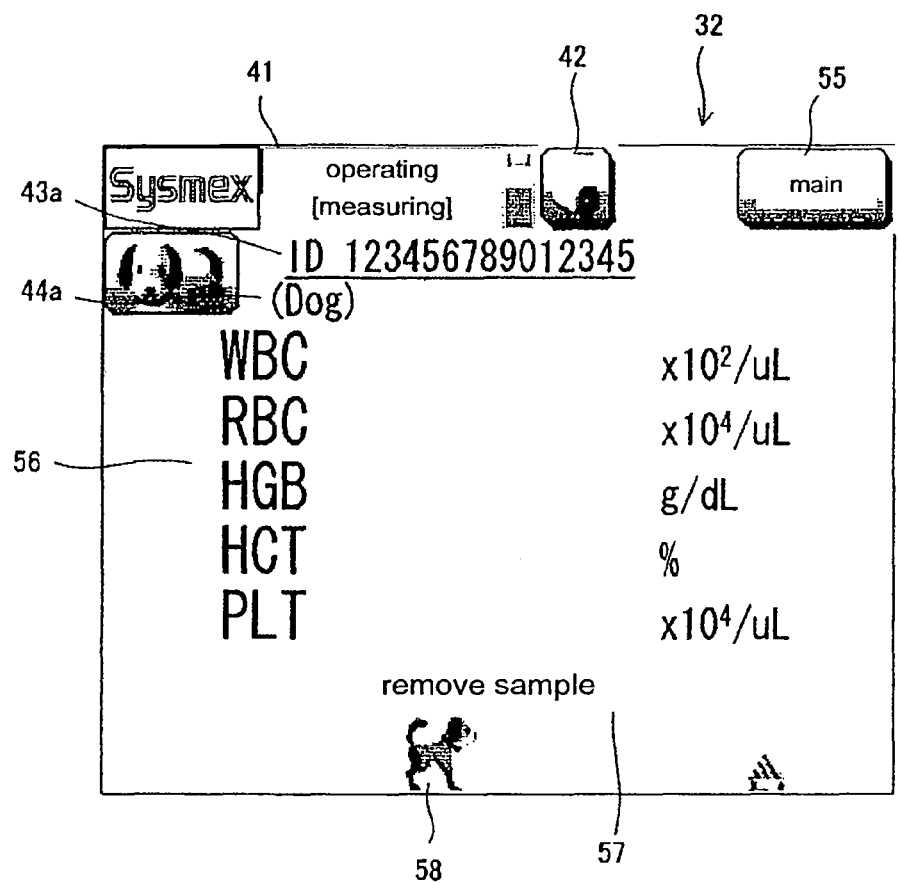
FIG. 7 shows screen during measurements.

The description now returns to the operation of the biological sample analyzer 1 with reference to the flow chart of FIG. 3. The controller 9 receives the instruction to start measurement (step S4: YES). When the user specifies the start of measurement by touching the start button 50 with a fingertip. When the start button 50 is selected in this way, the controller 9 starts the measurement operation and displays the measuring screen on the display 3 (step S5). The measuring operation can not be started, even though the start button 50 is selected, before receiving the species selection in step S3. FIG. 7 shows the screen during measurement. As shown in FIG. 7, the measuring screen 32 is, similar to the main screen 31, provided with an analyzer status display area 41 and paper feed button 42, as well as a species display area 44a, main screen call button 55, analysis result display area 56, message display area 57, and measurement operation progress status display area 58. The measuring screen 32 displays a line of text saying "Performing operation" in the analyzer status display area 41. When the user selects the main screen call button 55 in the measuring screen 32, the display of the display 3 is switched to the main screen 31. After the sample needed for measurement has been suctioned from the sample container, the message "Removing sample" is displayed in the message display area 57 as shown in the drawing. At this time, the user can open the sample panel 4 and remove the sample. The measurement operation progress status display area 58 is a band at the bottom edge of the screen, and the time needed for the measurement may be associated along the entire lateral length. That is, the left end can indicate the measurement starting time and the right end can indicate the measurement ending time, and the image of a dog can move from the left end to the right end in conjunction with the progress of the measurement operation. FIG. 7 shows the measuring screen in the dog analysis mode, and the display changes according to the species of animal being measured; that is, the image of a cat is shown to indicate the progress position in the cat analysis mode and the like.

When the measurement start in this way, blood cells in the sample are measured by the detecting part 17, and the measurement data D1 are stored in area 21b of the memory 21. Then, the controller 9 executes the sample analysis process using the measurement data D1 (step S7). This analysis process is executed under the analysis conditions according to the species of animal set in step S3.

Figure 8:
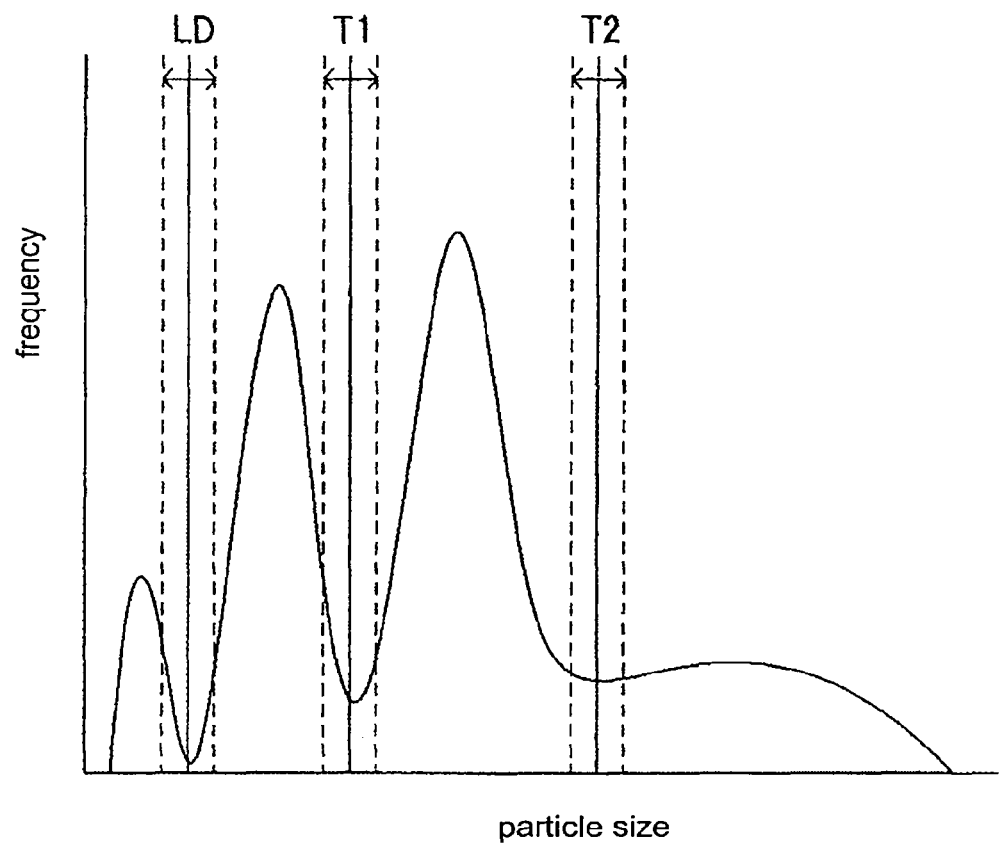
FIG. 8 is a graph showing an example of the particle size distribution of white blood cells in one species of animal.
Figure 9:
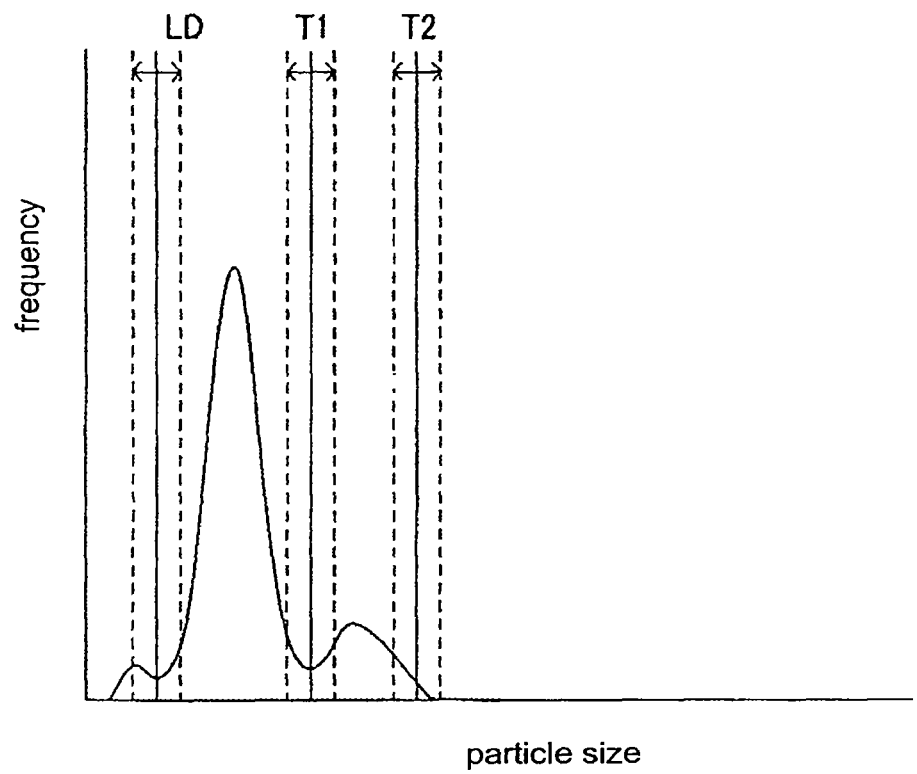
FIG. 9 is a graph showing an example of the particle size distribution of white blood cells in another species of animal.

The analysis of the sample by the biological sample analyzer 1 is described in detail below. A sample prepared by mixing a hemolytic agent with the blood sample is used in the measurement of white blood cells in the measuring mechanism 12. The electrical signal output from the detecting part 17 is a pulse signal that represents the size of the particle, and the measurement data D1 representing the size of the particle are obtained by signal processing the electrical signal. Therefore, it is possible to create a particle size distribution using the measurement data D1. FIG. 8 is a graph showing an example of a size distribution of white blood cells in one animal species (for example, dog), and FIG. 9 is a graph showing an example of a size distribution of white blood cells in another animal species (for example, rabbit). As shown in the drawings, the size distribution of the white blood cells differ markedly between the two different species of animals. This difference is due to the difference in the size of the white blood cells differs by species. When measuring white blood cells, the red blood cells are destroyed by adding hemolytic agent to the sample to eliminate the influence of red blood cells before measurement. The cell membrane of the destroyed red blood cells remain in the sample after the addition of the hemolytic agent, and these are measured together with the white blood calls. Furthermore, lymphocytes, monocyte, eosinophils, basophils, neutrophils and the like are present among the white blood cells, and these types have respectively difference particle sizes depending on the type. Therefore, in the analysis of white blood cells performed by the biological sample analyzer 1, the blood cells are classified, for example, as large white cells corresponding to neutrophils, monocytes, eosinophils, medium white cells corresponding to basophils, small white cells corresponding to lymphocytes, and red blood cell ghosts (cell membrane of the residual red blood cells). In the examples shown in FIGS. 8 and 9, white blood cells and red blood cell ghosts are classified by a first threshold LD, small white cells and medium white cells are classified by second threshold T1, and medium white cells and large white cells are classified by a third threshold T2. These thresholds differ depending on the species, and accurate analysis can not be performed unless the thresholds are appropriately set according to the species of animal being measured. More specifically, since the thresholds differ depending on the sample even in the same species of animal, a range is set for the threshold for each species of animal (indicated by the dashed line), and the trough position of the particle size distribution is searched within this range and the position of the trough obtained by this search is set as the threshold, as shown in FIGS. 8 and 9. In this case, an accurate threshold can not be obtained unless the search range of the threshold is set according to the species of animal. For this reason, the analysis conditions are preset for each species of animal in the biological sample analyzer 1, and when the measurement species is set, the analysis is executed pursuant with the analysis conditions for that animal species.

When the analysis process ends, the controller 9 stores the obtained analysis data D2 in area 21b of the memory 21 (step S8), the analysis results are printed on paper by the printer 11 (step S9), the main screen 31 is again displayed on the display 3 (step S10), and the next measurement is awaited. Since the analysis results are printed on paper by the printer 11, the user can easily confirm the analysis results. Furthermore, the user need not perform analysis of another species (step S11: NO) nor continue measurement when such is undesirable (step S12: NO), and may specify measurement after setting the next sample in the biological sample analyzer 1. Thus, it is possible to efficiently analyze a plurality of samples continuously without the user performing an operation to display the main screen 31 when starting the analysis of the next sample by switching the display automatically to the main screen 31.

It may happen that analysis is performed when a user erroneously sets a measurement object species due to an input error. When a plurality of samples are consecutively analyzed as described above, a plurality of species of animals may be included among the plurality of samples, such that a measurement object species is mistakenly entered. For example, when one cat sample is analyzed after consecutively analyzing dog samples, the user may forget to switch modes and fail to switch to the cat analysis mode after executing a plurality of analyses consecutively in the dog analysis mode. When a mistake of the measurement species has occurred, the user first selects the analysis result button 47 and specifies the display of the analysis result screen. When the instruction to display the analysis result screen is received (step S11: YES), the controller 9 displays the analysis result screen on the display 3 (step S13).

Figure 10:
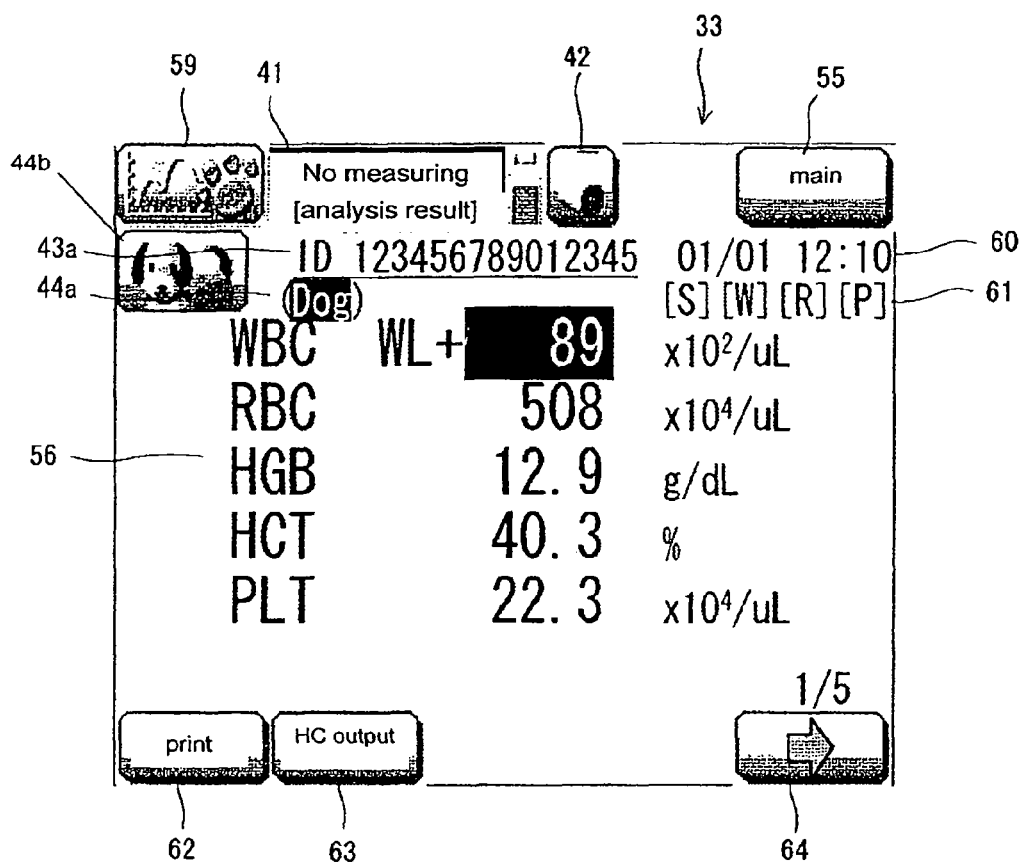
FIG. 10 shows an analysis result screen.

FIG. 10 shows an analysis result screen. The analysis result screen 33 is provided with an analyzer status display area 41, paper feed button 42, sample number display area 43a, animal species display area 44a, graphic image 44b representing the species of animal, main screen call button 55, and analysis result display area 56, as well as a manual analysis button 59, measurement date and time display area 60, manual analysis flag display area 61, print button 62, HC output button 63, and page switch button 64. Thus, the user can easily confirm the selected species of animal by displaying the species together with the analysis results, such that the possibility of the missing a species selection error is reduced. Although both the species display area 44a and graphic image 44b are displayed in the present embodiment, either one or the other alone may also be displayed.

A line of text saying "Measurement prevented" is displayed in the analyzer status display area 41 of the analysis result screen 33, indicating that measurement can not start. The measurement date and time is shown in a text display in the measurement day and time display area 60. The white blood cell concentration (WBC), red blood cell concentration (RBC), hemoglobin concentration (HGB), hematocrit value (HCT), and platelet concentration (PLT) obtained as analysis results are displayed in the analysis result display area 56. Among the analysis results, a flag 56a indicating an abnormality is displayed together with the value deviating from the proper range determined for each species of animal beforehand. Furthermore, a value changed by manual analysis, which is described later, is displayed with reverse text color and background. A user can confirm the analysis results on the display 3 by displaying the analysis result screen 33, which is beneficial for reconfirming whether or not there has been a setting error for the measurement species prior to performing the manual analysis. Furthermore, when the user selects the print button 62, the analysis results are printed on paper by the printer 11, and when the user selects the HC output button 63, the analysis results are sent to an external host computer (not shown in the drawing) that is connected to the biological sample analyzer 1. The manual analysis flag display area 61 is described later.

Figure 11:
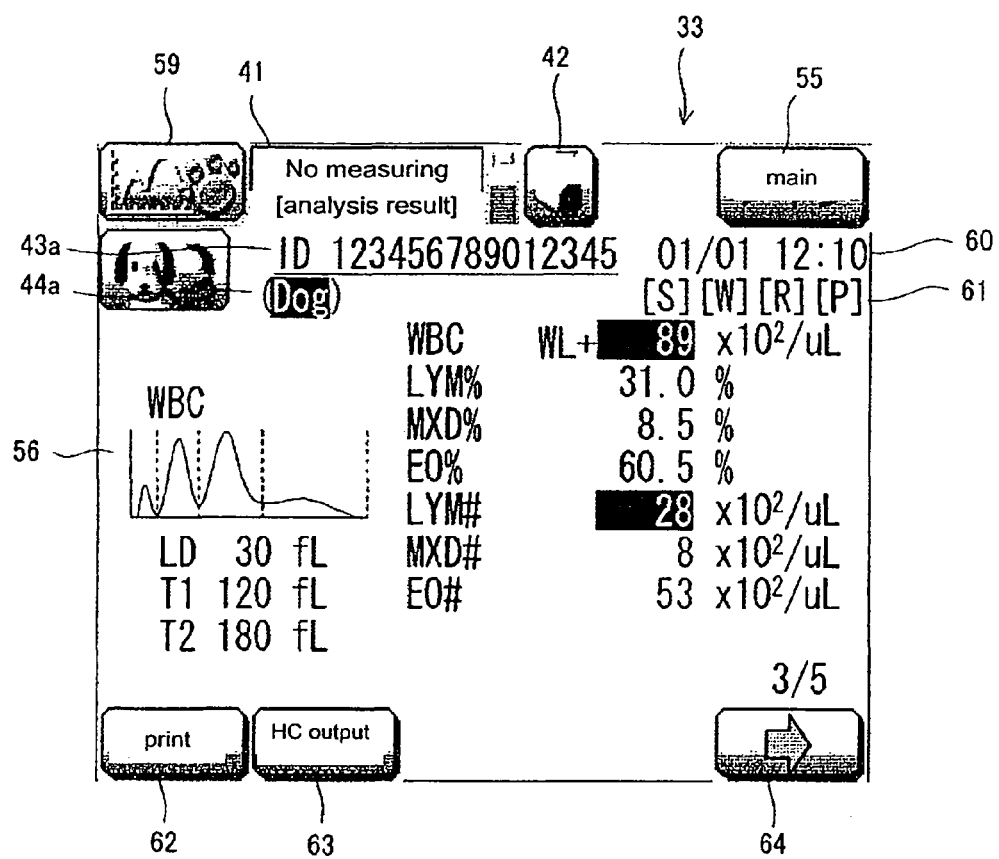
FIG. 11 shows another page of the analysis result screen.

The analysis result screen is provided with a plurality of pages, and a user can specify that a page should be switched by selecting the page switch button 64. The page is switched each time the page switch button 64 is pressed (selected). Therefore, the page switch button 64 may be pressed a plurality of times until the page desired by the user is displayed. FIG. 11 shows another page of the analysis result screen. FIG. 11 shows a page that displays detailed analysis results for white blood cells. This page displays the ratio and concentration for all components for each component of white blood cells in the analysis result display area 56. Numeric data and a particle size distribution charts are displayed, and the thresholds (LD, T1, T2) setting values are displayed below the particle size distribution charts. Although the detailed description is abbreviated, a page displaying general analysis results that displays the main items of the analysis results such as white blood cell concentration (WBC), red blood cell concentration (RBC), hemoglobin concentration (HGB), hematocrit value (HCT), and platelet concentration (PLT) as well as mean red blood cell volume (MCV), mean corpuscular cell hemoglobin (MCH), and mean corpuscular hemoglobin concentration (MCHC), a page displaying detailed analysis results for red blood cells, and a page displaying detailed analysis results for platelets are provided as other pages.

When the user requires a manual analysis, the user selects the manual analysis button 59 to specify the display of the manual analysis confirmation screen. When the instruction of the manual analysis execute confirmation screen is received (step S14: YES), the controller 9 displays the manual analysis confirmation screen on the display 3 (step S15).

Figure 12:
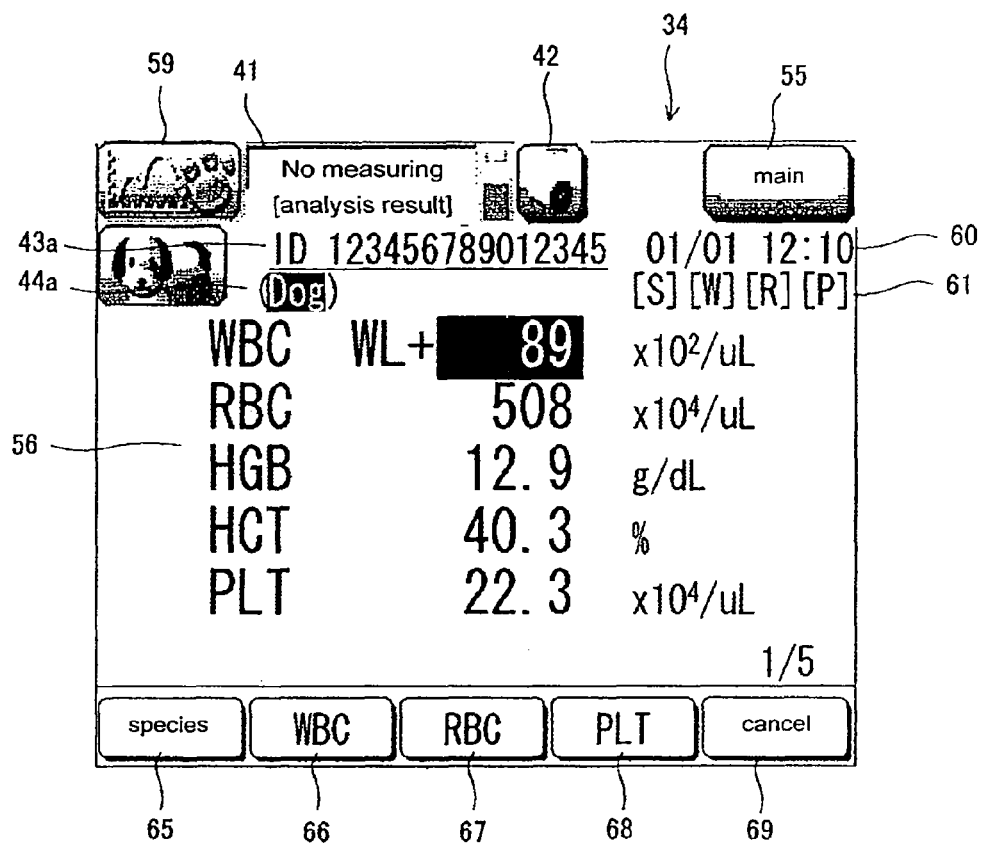
FIG. 12 shows a manual analysis execution confirmation screen.

FIG. 12 shows the manual analysis execution confirmation screen. The manual analysis confirmation screen 33 is, similar to the analysis result screen 33, provided with an analyzer status display area 41, paper feed button 42, sample number display area 43a, animal species display area 44a, main screen call button 55, and analysis result display area 56, measurement date and time display area 60, and manual analysis flag display area 61, as well as a species change button 65, WBC change button 66, RBC change button 67, PLT change button 68, and cancel button 69. The display of the analysis result display area 56 in the manual analysis confirmation screen 34 is identical to the display in the analysis result screen 33, and further description is omitted. The species change button 65 is used to change the setting of the species of animal, the WBC change button 66 is used to change the setting of the white blood cell analysis conditions (thresholds), the RBC change button 67 is used to change the red blood cell analysis conditions (thresholds), and the PLT change button 68 is used to change the platelet analysis conditions (thresholds). When a user changes the setting of the analysis conditions of the measurement species, white blood cell, red blood cell, or platelet, the set values can be changed by selecting the appropriate button. When a user does not perform reanalysis, the cancel button 69 is selected to return to the process of step S13, and return to the display on the analysis result screen 33. When one of the buttons 65 through 68 is selected (step S16: "Manual analysis screen display instruction," the controller 9 displays the manual analysis screen used in the reanalysis and "hanging the setting value on the display 3 (step S17).

Figure 13:
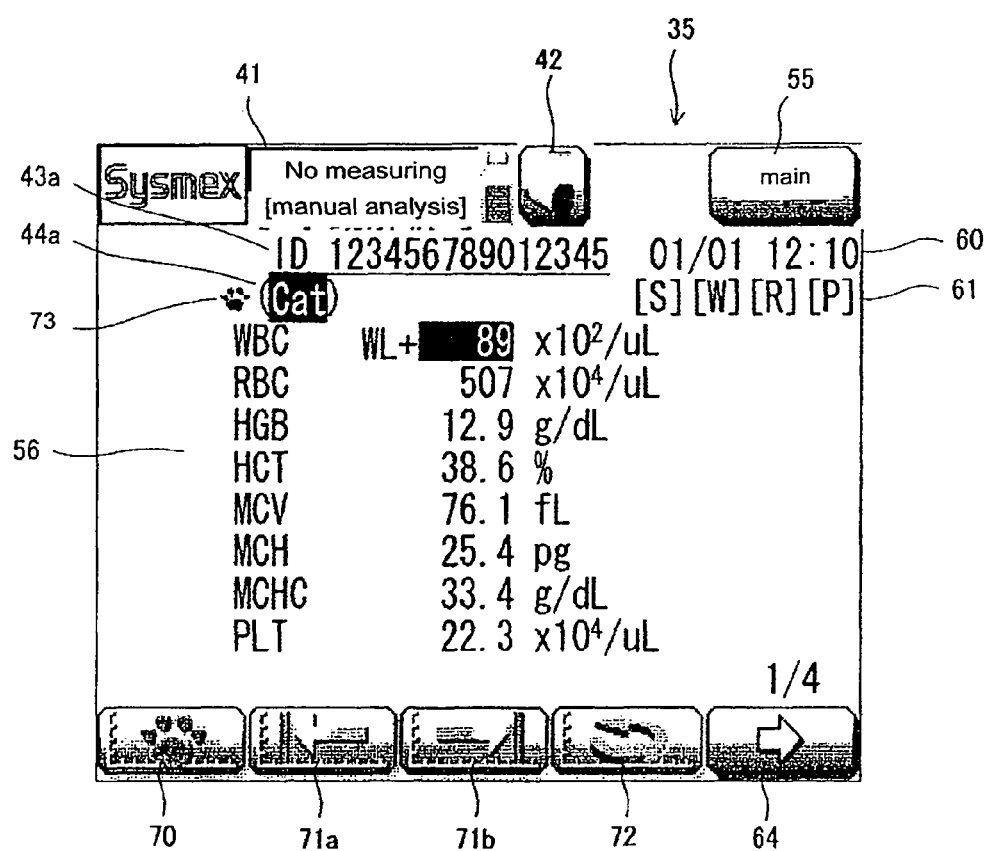
FIG. 13 shows a manual analysis screen.

FIG. 13 shows a manual analysis screen similar to the analysis result screen 33, the manual analysis screen 33 is provided with an analyzer status display area 41, paper feed button 42, sample number display area 43a, animal species display area 44a, main screen call button 55, and analysis result display area 56, measurement date and time display area 60, and manual analysis flag display area 61, and page change button 64, as well as a manual analysis item selection button 70, change buttons 71a and 71b, and reanalyze button 72 similar to the analysis result screen 33, the manual analysis screen 33 is provided with a plurality of pages (a page for general analysis results, a page for detailed analysis results for white blood cells, a page for detailed analysis results for red blood cells, and a page for detailed analysis results for platelets), such that a user switches the page by selecting the switch page button. The display of the analysis results display area 56 in the manual analysis screen 35 is identical to the display in the analysis result screen 33, and therefore further description is omitted. The user can change the set values of the analysis conditions of the measurement species, white blood cells, red blood cells, or platelets, and can execute reanalysis using the manual analysis screen 35.

Changing the measurement species and set values of the analysis conditions is accomplished as described below. Changing the setting of the measurement species can be accomplished on the pages of all manual analysis screens. When the species change button 65 is selected in the manual analysis confirmation screen 34, a pad icon 73 is displayed on the left side of the species display area 44a indicating is it possible to change the setting to the measurement species. At this time, the change buttons 71a and 71b are used to select the species of the animal. As shown in the drawing, a left point arrow is displayed on the change button 71a and a right pointing arrow is displayed on the change button 71b. Whenever the change button 71a us touched by the fingertip of the user, the species name displayed in the species display area 44a is switched one by one in a predetermined order to indicate the set measurement species has changed. When the change button 71b is touched by the fingertip of a user, the animal species is switched in the reverse order. The measurement species is changed by the fingertip of the user touching the change buttons 71a and 71b until the name of the desired species is displayed. When the measurement species is changed in this way, the analysis conditions are set in correspondence to the measurement species.

Changing the setting of the analysis conditions of the white blood cells is possible only on the page of the detailed analysis results of the white blood cells on the manual analysis screen; changing the setting of the analysis condition of the red blood cells is possible only on the page of the detailed analysis results of the red blood cells; and changing the setting of the analysis conditions of the platelets is possible only on the page of detailed analysis results of the platelets. Although only changing the setting of the analysis conditions of white blood cells is described here, the settings of the analysis conditions of the red blood cells and platelets can be changed in the same way. When changing the setting of the analysis conditions of white blood cells, the user displays the page of detailed analysis results of white blood cells on the manual analysis screen. When the WBC change button 66 is selected on the manual analysis confirmation screen 34, the pad icon 73 is displayed on the left side of the set value indicating that it is possible to change the setting of the threshold. In this initial state, LD is selected from among the three thresholds LD, T1, and T2. At this time, the selected threshold is switched in the sequence T1, T2, LD each time the fingertip of the user touches the manual analysis item selection button 70. Also at this time, the change buttons 71a and 71b are used to change the set value of the threshold. The set value of the selected threshold decreases each time the fingertip of the user touches the change button 71a, and the set value of the selected threshold increase each time the fingertip of the user touches the change button 71b. The user touches the change buttons 71a and 71b with a fingertip until the threshold is set at a desired setting value in order to change the analysis condition setting.

When the controller 9 receives the change of the set measurement species or the change of the set analysis conditions (step S18: YES), an instruction to execute reanalysis is awaited (step S19). The reanalysis execution instruction is accomplished when the user selects the reanalysis button 72. When the controller 9 receives the reanalysis execution instruction from the user (step S19: YES), the controller 9 executes reanalysis according to the changed analysis conditions (step S20). In this process, analysis is performed under the newly set analysis conditions using the measurement data D1 store din the area 21b of the memory 21. Therefore, it is not necessary to prepare a sample by aspirating a new sample, thereby preventing needless waste of valuable sample. For example, even when sample remains in the sample container, when this sample is used for reanalysis, another sample must be collected in the event that a further analysis is required. Furthermore, yet another sample must be collected when an insufficient amount of sample remains in the sample container. There are many small animals from whom multiple sample can not be collected, and great stress is put on the bodies of these small animals each time another sample is collected from them. Such samples are very valuable, and preventing the wasteful consumption of these samples is very important in biological sample analysis. Furthermore, even when reanalysis is not performed after a sample has been aspirated, the measurement data of a previous analysis can be used in analysis, thereby reducing the time involved and reducing the labor.

When the measurement species is changed and reanalysis performed, a flag "S" is displayed in the manual analysis flag display area 61; a flag "W" is displayed when the setting of the white blood cell analysis conditions (thresholds) are changed and reanalysis is performed; a flag "R" is displayed when the setting of the red blood cell analysis conditions (thresholds) are changed and reanalysis is performed; and a flag "P" is displayed when the setting of the platelet analysis conditions (thresholds) are changed and reanalysis is performed.

When the reanalysis process ends and the selection of the main screen call button 55 is received from a user (step S21: YES), the controller 9 displays a screen for determining whether or not to save the results of the reanalysis, and instructions are received from the user (step S22). When an instruction to save the results of the reanalysis are received in step S22 (step S22: YES), the controller 9 stores the obtained analysis data D2 in the area 21b of the memory 21 (step S23), the printer 11 prints the analysis results on paper (step S24), and the controller returns the process to step S12. Furthermore, when an instruction not to save the result is received in step S22 (step S22: NO), the controller 9 returns the process to step S12.

When the user wants to end the analysis of a sample in the biological sample analyzer 1, the user touches the shutdown button 48 on the main screen 31 using a fingertip. When the selection of the shutdown button 48 is received in this way (step S12: YES), the controller 9 stops the biological sample analyzer 1.

Although the description has been abbreviated by simplification in the present embodiment, it is possible to reanalyze the analysis data D stored in the memory 21 at any time.

Although the present embodiment has been described in terms of a continuous sequence of operations of obtaining measurement data D1 and execution of an analysis process from a prepared measurement sample after the measurement species has been set, the present invention is not limited to this sequence inasmuch as, for example, the measurement data D1 can be acquired beforehand without setting the measurement species, and thereafter setting a suitable measurement species before performing analysis.

Although the species of animal is selected before the instruction to start a measurement has been received in the present embodiment, the present invention is not limited to this sequence inasmuch as, for example, a default species may be set beforehand, such that the measurement data D1 can be analyzed at the default species setting without selecting a species.

Although the biological sample analyzer 1 analyzes blood particles in the present embodiment, the present invention is not limited to this analysis inasmuch as, for example, the present invention is also applicable to apparatuses that perform blood coagulation measurements, immunological analysis and urine analysis.

What is claimed is:
1. A sample analyzer comprising:
(a) a measurement section that interrogates a sample of a patient animal, wherein e sample is prepared for a test in which a particular type of blood cells in the sample is targetedly analyzed;
(b) a memory that stores cell size criteria for the targeted blood cells in relation to a respective of multiple different animal species, wherein the cell size criteria for the targeted blood cells are for discriminating the targeted blood cells by cell sizes; and
a controller programmed to:
(c) receive a first selection of animal species;
(d) operate the measurement section to obtain a size distribution of the target blood cells in the sample;
(e) store the obtained size distribution in the memory;
(f) retrieve from the memory a first of the cell size criteria for the target blood cells stored in relation to the animal species of the first selection;
(g) apply, to the stored size distribution, the first of the cell size criteria for the target blood cells to discriminate the target blood cells in the sample by cell sizes; and
(h) as a test result of the test for the sample, store in the memory counts of respective discriminated target blood cells;
(i) display the test result for the sample, along with a representation of the animal species of the first selection and a manual analysis button for initiating a reanalysis process in which the animal species of the first selection is corrected and the stored size distribution in the memory is re-evaluated without using the sample or obtaining another sample from the patient animal;
(j) responsive to an operation of the manual analysis button, display a plurality of different animal species selectable to correct the animal species of the first selection;
(k) in the reanalysis process, receive a second selection of animal species, wherein the animal species of the second selection is different from the animal species of the first selection;
(l) in the reanalysis process, retrieve the stored size distribution from the memory;

(m) in the reanalysis process, retrieve from the memory a second of the cell size criteria for the target blood cells stored in relation to the animal species of the second selection;

(n) in the reanalysis process, apply, to the retrieved size distribution for a second time, the second of the cell size criteria for the target blood cells to re-discriminate the target blood cells by cell sizes; and (o) in the reanalysis process, as a correct result for the test for the sample, store counts of respective re-discriminated target blood cells over the test result for the sample already stored in the memory.

2. The sample analyzer of claim 1, wherein the plurality of different animal species comprise a dog, a cat, a cow, a horse, a pig, a sheep, a goat, a deer, a mouse, and a rabbit.

3. The sample analyzer of claim 1, wherein the controller displays a start request button for requesting for starting the test of the sample.

4. The sample analyzer of claim 1, wherein the controller displays a plurality of different animal species for selecting the animal species of the first selection.

5. A sample analyzing method comprising:
(a) interrogating a sample from a patient animal by a measurement section, wherein the sample is prepared for a test in which a particular type of blood cells in the sample is targetedly analyzed;
(b) storing in a memory cell size criteria for the tar et blood cells in relation to a respective of multiple different animal species, wherein the cell size criteria for the target blood cells are for discriminating the target blood cells by cell sizes;
(c) receiving a first selection of animal species;
(d) operating the measurement section to obtain a size distribution of the target blood cells in the sample;
(e) storing the obtained size distribution in the memory;
(f) retrieving from the memory a first of the cell size criteria for the target blood cells stored in relation to the animal species of the first selection;
(g) applying, to the stored size distribution, the first of the cell size criteria for the target blood cells to discriminate the target blood cells in the sample by cell sizes; and
(h) as a test result of the test for the sample, storing in the memory counts of respective discriminated target blood cells;
(i) displaying the test result for the sample, along with a representation of the animal species of the first selection and a manual analysis button for initiating a reanalysis process in which the animal species of the first selection is corrected and the stored size distribution in the memory is re-evaluated without using the sample or obtaining another sample from the patient animal; and
(j) responsive to an operation of the manual analysis button, displaying a plurality of different animal species selectable to correct the animal species of the first selection;
(k) in the reanalysis process, receiving a second selection of animal species which is different from the first animal species of the first selection;
(l) in the reanalysis process, retrieving the stored size distribution from the memory;
(m) in the reanalysis process, retrieving from the memory a second of the cell size criteria for the target blood cells stored in relation to the animal species of the second selection;
(n) in the reanalysis process, applying, to the retrieved size distribution for a second time, the second of the cell size criteria for the target blood cells to re-discriminate the target blood cells by cell sizes; and
(o) in the reanalysis process, as a correct result of the test for the sample, storing counts of respective re-discriminated target blood cells over the test result for the sample already stored in the memory.

6. The sample analyzing method of claim 5, wherein the plurality of different animal species comprise a dog, a cat, a cow, a horse, a pig, a sheep, a goat, a deer, a mouse, and a rabbit.

7. The sample analyzing method of claim 5, further comprising displaying a plurality of different animal species for selecting the animal species of the first selection.

8. The sample analyzer according to claim 1, wherein in performing operation (j), the controller, responsive to an operation of the manual analysis button, displays a species button to initiate a selection of a correct species.

9. The sample analyzer according to claim 8, wherein the controller, responsive to an operation of the species button, displays a plurality of selectable animal species for selection.

10. The sample analyzer according to claim 1, wherein the target blood cells are white blood cells.

11. The sample analyzer according to claim 10, wherein the cell size criteria for the white blood cells comprise a first threshold value (LD) for discriminating white blood cells and red blood cell ghosts, a second threshold (T1) for discriminating small white cells and medium white cells, and a third threshold (T2) for discriminating the medium white cells and large white cells.

12. The sample analyzer according to claim 1, wherein the representation of the animal species of the first selection comprises at least one of a graphical image of and a text representing the animal species of the first selection.

13. The sample analyzer according to claim 1, where the controller is further programmed to display a flag for notifying that the species of the first selection is corrected to the species of the second selection and the size distribution is re-evaluated with the second of the cell size criteria for the target blood cells.

14. The sample analyzing method according to claim 5, wherein step (j) comprises displaying, responsive to an operation of the manual analysis button, a species button to initiate a selection of a correct species.

15. The sample analyzing method according to claim 14, wherein step (j) further comprises displaying, responsive to an operation of the species button, a plurality of selectable animal species for selection.

16. The sample analyzing method according to claim 5, wherein the target blood cells are white blood cells.

17. The sample analyzing method according to claim 16, wherein the cell size criteria for the white blood cells comprise a first threshold value (LD) for discriminating white blood cells and red blood cell ghosts, a second threshold (T1) for discriminating small white cells and medium white cells, and a third threshold (T2) for discriminating the medium white cells and large white cells.

18. The sample analyzing method according to claim 5, wherein the representation of the animal species of the first selection comprises at least one of a graphical image of and a text representing the animal species of the first selection.

19. The sample analyzing method according to claim 5, further comprising displaying a flag for notifying that the species of the first selection was corrected to the species of the second selection and the size distribution information is re-evaluated with the second of the cell size criteria for the particular cell type.

* * * * *

UNITED STATES PATENT AND TRADEMARK OFFICE
CERTIFICATE OF CORRECTION

PATENT NO. : 8,958,990 B2  Page 1 of 1
APPLICATION NO. : 11/542312
DATED : February 17, 2015
INVENTOR(S) : Hideki Hirayama It is certified that error appears in the above-identified patent and that said Letters Patent is hereby corrected as shown below:

In the Claims

In column 15, claim 5, line 27, after "criteria for the" replace "tar et" with --target--.

In column 15, claim 5, line 41, after "by cell sizes;" delete "and".

In column 15, claim 5, line 51, after "the patient animal;" delete "and".

Signed and Sealed this
Tenth Day of November, 2015

Michelle K. Lee
*Director of the United States Patent and Trademark Office*